United States Patent [19]

Lee

[11] 4,086,236

[45] Apr. 25, 1978

[54] 6,7-METHYLENEDIOXY-1-(2,2,2-TRIFLUOROETHYL)-4(1H)-QUINOLONE-3-CARBOXYLIC ACID

[75] Inventor: Kyu Tai Lee, Wilmington, Del.

[73] Assignee: E. I. Du Pont de Nemours and Company, Wilmington, Del.

[21] Appl. No.: 747,732

[22] Filed: Dec. 6, 1976

Related U.S. Application Data

[63] Continuation-in-part of Ser. No. 578,137, May 16, 1975, Pat. No. 4,036,962, which is a continuation-in-part of Ser. No. 496,851, Aug. 12, 1974, abandoned.

[51] Int. Cl.² ............................................. C07D 491/04
[52] U.S. Cl. ............................................. 260/287 AN
[58] Field of Search ................................. 260/287 AN

[56] References Cited

U.S. PATENT DOCUMENTS 3,287,458  11/1966  Kominsky ................... 260/287 AN

OTHER PUBLICATIONS

Yale, "Journal of Med. and Pharm. Chem.," 1959, pp. 121 and 131.

*Primary Examiner*—Donald G. Daus
*Assistant Examiner*—David E. Wheeler

[57] ABSTRACT

Certain esters of 6,7-methylenedioxy-1-(2,2,2-trifluoroethyl)-4(1H)-quinolone-3-carboxylic acid, such as the trimethylacetoxymethyl ester, useful as antibacterials.

2 Claims, No Drawings

6,7-METHYLENEDIOXY-1-(2,2,2-TRIFLUOROETHYL)-4(1H)-QUINOLONE-3-CARBOXYLIC ACID

CROSS-REFERENCE TO RELATED APPLICATIONS

This application is a continuation-in-part of copending application Ser. No. 578,137, filed May 16, 1975 now U.S. Pat. No. 4,036,962 July 19, 1977 which is a continuation-in-part of application Ser. No. 496,851, filed Aug. 12, 1974, now abandoned.

BACKGROUND

This invention relates to quinoline derivative antibacterials.

Kaminsky, in U.S. Pat. No. 3,287,458, discloses antibacterial, 6,7-methylenedioxy-1,4-dihydro-4-oxoquinolinecarboxylic acids substituted in the 1 position with lower alkyl or a variety of other substituents. The compound where this substituent is ethyl is commonly known as oxolinic acid.

Oxolinic acid is a highly effective antibacterial agent, but a high incidence of undesirable side effects is reported. Cox, Claire E., *Delaware Medical Journal*, November 1970, p. 327, and Kershaw and Leigh (*Journal of Antimicrobial Therapy* 1, 311–315, 1975) have indicated that because of toxicity, "it should not be used as a first-line drug in the therapy of urinary tract infections."

Another quinoline derivative which is now marketed for the treatment of urinary tract infections is nalidixic acid. It was originally shown to be effective for this use; however, further experience with nalidixic acid has suggested that its usefulness may be limited by its tendency to rapidly evoke bacterial resistance. Ronald, A. R. et al. New England Journal of Medicine, 275:1081–1088 (1966). Moreover, a relatively high incidence of side effects also occurs with nalidixic acid administration. Cox, p. 327.

Thus, there is a continuing need for safe and effective antibacterials; especially because strains of bacteria can develop that are resistant or immune to antibacterials now being used.

SUMMARY

According to this invention, there is provided compounds of Formula I, pharmaceutical compositions containing them, and methods of using them to treat bacterial infections in mammals.

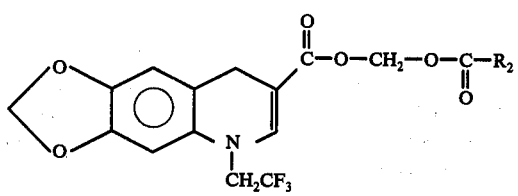

where $R_2$ = primary, secondary, or tertiary alkyl of 1-10 carbons, cycloalkyl from 3-10 carbons, or phenyl.

Also provided are compounds of the following formula, which are useful as intermediates for making the antibacterials of this invention;

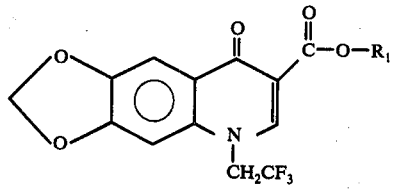

where $R_1$ = H, alkyl of 1-3 carbons or a univalent cation: $Na^+$, $K^+$, $NH_4^+$, $Li^+$, $\frac{1}{2}Ca^{++}$, $\frac{1}{2}Mg^{++}$.

DETAILED DESCRIPTION OF THE INVENTION

Preferred Compounds

Compounds preferred for their activity are those where $R_2$ is tertiary alkyl, especially tertiary butyl. The most preferred compound is 6,7-methylenedioxy-1-(2,2,2-trifluoroethyl)-4(1H)-quinolone-3-carboxylic acid, trimethylacetoxymethyl ester.

Synthesis

Synthesis of intermediates starts with the reaction between 3,4-methylenedioxyaniline and the 2,2,2-trifluoroethyl ester of trichloromethanesulfonic acid (J. Med. Chem., 16, 1360 (1973)) in the presence of an acid-scavenger such as triethylamine or pyridine. The reaction is carried out in an inert solvent such as toluene or benzene at elevated temperature of 50° to 200° C., preferably 80°-130° C. The resulting trifluoroethylaniline is isolated in pure form by distillation.

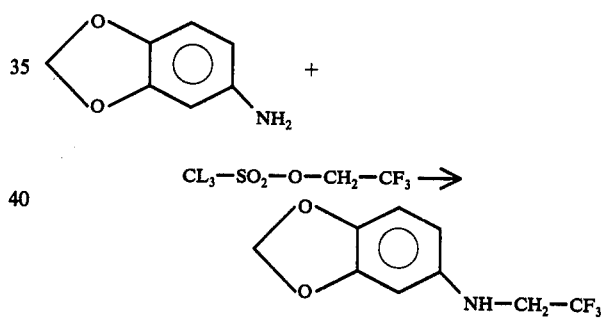

It is then reacted with diethyl ethoxymethylenemalonate at 100°–200° C., preferably 140°–150° C. or 1–10 hours. The resulting adduct, diethyl[3,4-methylenedioxy-N-(2,2,2-trifluoroethyl)]anilinomethylenemalonate, is usually a viscous oil, but pure enough to be used for the next reaction without further purification.

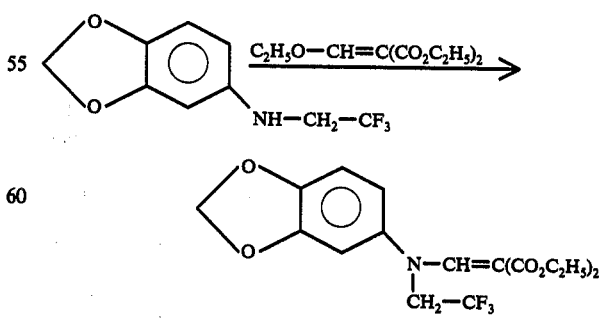

The ring closure of the malonate adduct is accomplished by mixing it in polyphosphoric acid and heating at 100°–140° C., usually 115°–120° C. for between 20 and 60 minutes. The mixture is diluted with ice water and the solid product, 6,7-methylenedioxy-1-(2,2,2-trifluoroethyl)-4(1H)-quinolones-3-carboxylic acid, ethyl ester, is isolated.

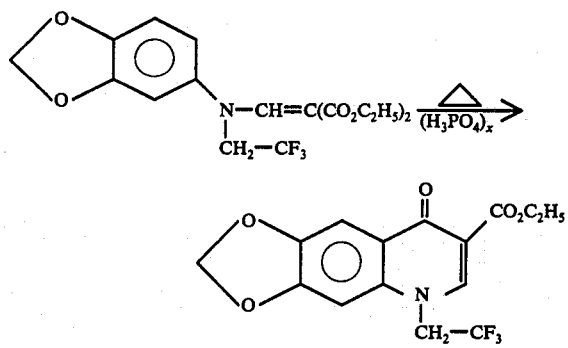

The ring closure can also be done by treating the malonate adduct with phosphorous oxychloride, or phosphorous pentachloride in nitrobenzene, or with boron trifluoride etherate, or polyphosphate ester.

The ethyl ester is hydrolyzed in aqueous acid such as 6N hydrochloric acid or 6N sulfuric acid at elevated temperature. The reaction is usually completed in 1 to 5 hours to give the product 6,7-methylenedioxy-1-(2,2,2-trifluoroethyl)-4(1H)-quinolone-3-carboxylic acid.

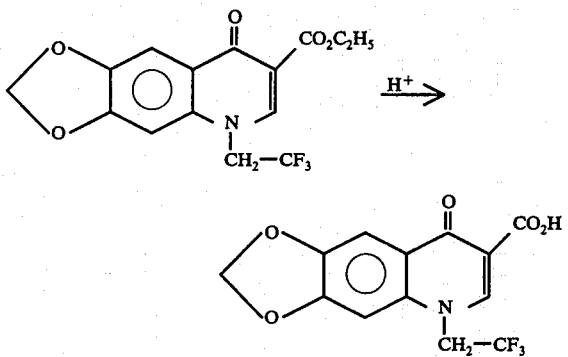

An alternate method of synthesis of 6,7-methylenedioxy-1-(2,2,2-trifluoroethyl)-4(1H)-quinolone-3-carboxylic acid involves the trifluoro-ethylation of 1,4-dihydro-6,7-methylenedioxy-4-oxo-3-carboxylic acid, ethyl ester (J. Med. Chem. 11, 160 (1968)) with the 2,2,2-trifluoroethyl ester of trichloromethanesulfonic acid. A strong base such as sodium hydride or potassium tertiary butoxide is used to generate anion and the reaction is carried out in an inert polar solvent, preferably dimethyl formamide or dimethyl sulfoxide. The ethyl ester derived is again hydrolyzed to give the final product.

The salts of the acid intermediates are prepared by mixing a dimethyl formamide solution of the acid with equivalent amount of aqueous base (ammonium hydroxide or other alkaline hydroxide). The resulting mixture is then diluted with ethanol and the solid salts are isolated by filtration. This reaction is reversible, therefore, the acid can be obtained from the salt.

The antibacterial esters are prepared by reacting the 6,7-methylenedioxy-1-(2,2,2-trifluoroethyl)-4(1H)-quinolone-3-carboxylic acid with the chloromethyl ester of an appropriate carboxylic acid, such as chloromethyl trimethylacetate, in the presence of a base, such as triethylamine or potassium carbonate. Suitable solvents for this reaction are dimethyl formamide or dimethyl sulfoxide.

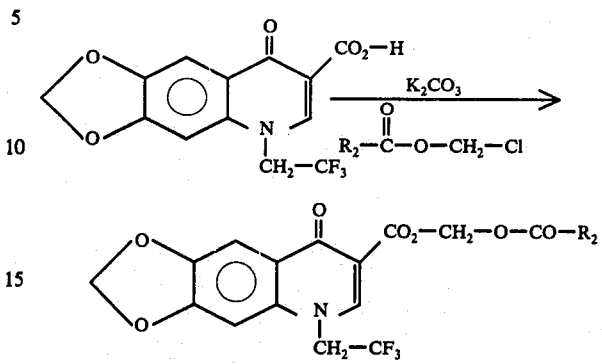

Example 1

A. 3,4-Methylenedioxy-N-(2,2,2-trifluoroethyl)aniline

A mixture of 7 g. (0.051 mole) of 3,4-methylenedioxyaniline, 14.5 g. (0.051 mole) of 2,2,2-trifluoroethyl trichloromethanesulfonate, and 5.2 g (0.052 mole) of triethylamine in 60 ml. of toluene was heated under reflux for 3 1/2 hours. The cooled mixture was washed with water, dried over anhydrous magnesium sulfate, and concentrated under reduced pressure. The oily residue is distilled (b.p. 1.9 mm. 103°-5°) to give pure 3,4-methylenedioxy-N-(2,2,2-trifluoroethyl)-aniline.

B. Diethyl [3,4-methylenedioxy-N-(2,2,2-trifluoroethyl)]anilinomethylene malonate A mixture of 18 g. (0.0823 mole) of the aniline obtained in Part A and 17.8 g. (0.0823 mole) of diethyl ethoxymethylenemalonate was heated to 140°–150° C. until the evolution of ethanol ceases (about 3-4 hours). The viscous oily product is pure enough to be used without further purification.

C. 6,7-Methylenedioxy-1-(2,2,2-trifluoroethyl)-4(1H)-quinolone-3-carboxylic acid, ethyl ester A mixture of 10 g. of the malonate obtained in Part B and 50 g. of polyphosphoric acid was heated at 115°–120° C. for 25 minutes with stirring. The mixture was then poured into 500 ml. of ice water. The pH was adjusted to about 2 by adding 50% sodium hydroxide solution and the solid was collected by filtration. The solid, the acid ester, was recrystallized from ethyl acetate-diethyl ether mixture and then with ethanol, m.p.: 204°–6° C.

Anal. calc'd. for $C_{15}H_{12}F_3NO_5$; C: 52.48; H: 3.52; N: 4.08. Found: C: 52.47; H: 3.68; N: 4,18.

D. 6,7-Methylenedioxy-1-(2,2,2-trifluoroethyl)-4(1H)-quinolone 3-carboxylic acid A mixture of 1 g. of the ethyl ester obtained in Part C and 40 ml of 6N hydrochloric acid was heated under reflux for 1 1/2 hours. The mixture was cooled and the solid product was collected by filtration and washed with water and dried under reduced pressure, m.p. 323°–5° C. (dec.).

Anal. calc'd for $C_{13}H_8F_3NO_5$: C: 49.54; H: 2.56; N: 4.45. Found: C: 49.44; H: 2.58; N: 4.49.

Example 2

6,7-Methylenedioxy-1-(2,2,2-trifluoroethyl)-4(1H)-quinolone-3-carboxylic acid

A mixture of 15.6 (0.06 mole) of 6,7-methylenedioxy-4(1H)-quinolone-3-carboxylic acid (J. Med. Chem. 11, 160 (1968)) and 1.5 g. (0.062 mole) of sodium hydride powder in 250 ml. of dimethyl formamide was heated with stirring for 0.5 hour at 80°–90° C. 2,2,2-Trifluoroethyl trichloromethanesulfonate (17.5 g. 0.62 mole) was then added dropwise. The temperature was maintained at 80°–90° for an additional two hours. The cooled mixture was poured into ice water and the solid product was isolated by filtration. It was recrystallized from ethanol. This product was identical to that obtained from Example 1.

Example 3

6,7-Methylenedioxy-1-(2,2,2-trifluoroethyl)-4(1H)-quinolone-3-carboxylic acid, trimethylacetoxymethyl ester To a mixture of 2.6 g. 6,7-methylenedioxy-1-(2,2,2-trifluoroethyl)-4(1H)-quinolone-3-carboxylic acid and 35 ml. of dimethyl formamide was added 1.4 g. of triethylamine. The mixture was warmed to 55° and kept there for ½ hour. 2.8 g. of chloromethyl trimethylacetate was then added and the resulting mixture was stirred at 55° for 5 hours. The cooled solution was diluted with 150 ml. of ethyl acetate and washed with water. The ethyl acetate solution was dried over magnesium sulfate and concentrated. The solid residue, 6,7-methylenedioxy-1-(2,2,2-trifluoroethyl)-4(1H)-quinolone-3-carboxylic acid, trimethylacetoxymethyl ester, was recrystallized from $CH_2Cl_2$-ether mixture; m.p. 190°–1°.

Anal. Calc'd. for $C_{19}H_{18}F_3NO_7$: C: 53.15; H: 4.23; N: 3.26. Found: C: 53.14; H: 4.20; N: 3.24.

The ester thus obtained was found to be the metastable crystalline form. Thus, when this compound was recrystallized from high boiling solvent such as acetonitrile or ethyl acetate, or when it was left at room temperature for a long time, a different crystalline ester (more stable) was obtained: m.p. 199°—200°.

Anal. Calc'd. for $C_{19}H_{18}F_3NO_7$: C: 53.15; H: 4.23; N: 3.26. Found: C: 53.55; H: 4.38; N: 3.52.

The nmr spectra of the two esters are identical. Biologically, the stable form was found to be less active than the meta-stable, probably due to absorption differences.

The procedure of Example 3 can be repeated using the appropriate chloromethyl ester in place of chloromethyl trimethylacetate to give the following compounds:

| Example | Chloromethyl Ester | Compound |
|---|---|---|
| 4 | chloromethyl isobutyrate | 6,7-methylenedioxy-1-(2,2,2-trifluoroethyl)-4(1H)-quinolone-3-carboxylic acid, isobutyryloxymethyl ester m.p. 169–171° |
| 5 | chloromethyl 2,2-dimethyl-n-butyrate | 6,7-methylenedioxy-1-(2,2,2-trifluoroethyl)-4(1H)-quinolone-3-carboxylic acid, 2,2-dimethyl-n-butyryloxymethyl ester, m.p. 169–170° |
| 6 | chloromethyl n-hexanoate | 6,7-methylenedioxy-1-(2,2,2-trifluoroethyl)-4(1H)-quinolone-3-carboxylic acid, n-hexanoyloxymethyl ester, m.p. 113–5° |
| 7 | chloromethyl n-decanoate | 6,7-methylenedioxy-1-(2,2,2-trifluoroethyl)-4(1H)-quinolone-3-carboxylic acid, n-decanoyloxymethyl ester, m.p. 119–120° |
| 8 | chloromethyl cyclohexanecarboxylate | 6,7-methylenedioxy-1-(2,2,2-trifluoroethyl)-4(1H)-quinolone-3-carboxylic acid, cyclohexanecarbonyloxymethyl ester, m.p. 176–8° |
| 9 | chloromethyl benzoate | 6,7-methylenedioxy-1-(2,2,2-trifluoroethyl)-4(1H)-quinolone-3-carboxylic acid, benzoyloxymethyl ester, m.p. 192–4° |

Example 10

To a mixture of 2.6 g. of 6,7-methylenedioxy-1-(2,2,2-trifluoroethyl)-4(1H)-quinolone-3-carboxylic acid and 35 ml. of dimethyl formamide was added 1.4 g. of potassium carbonate. The mixture was stirred at room temperature for ½ hour and 3 g. of chloromethyl trimethylacetate was added. The resulting mixture was stirred at room temperature for 3 days and poured into 200 ml. of water. The solid precipitate was collected by filtration and dissolved in $CH_2Cl_2$. The $CH_2Cl_2$ solution was dried over anhydrous magnesium sulfate and concentrated to give a solid product, which is identical to that obtained in Example 3.

Dosage Forms and Use

The antibacterial agents of this invention can be administered to exert their antibacterial activity by any means that produces contact of the active agent with the site of infection in the body of a mammal. They can be administered by any conventional means available for use in conjunction with pharmaceuticals; either as individual therapeutic agents or in a combination of therapeutic agents. They can be administered along, but are generally administered with a pharmaceutical carrier selected on the basis of the chosen route of administration and standard pharmaceutical practice.

These compounds exhibit potent antibacterial activity, particularly against such gram-negative bacteria as the Escherichia group and Proteus group; also against such gram positive bacteria as the Staphlococcus and Bacillus groups.

The dosage administered will, or course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Effective antibacterial amount: usually a daily dosage of active ingredient can be about 5 to 100 milligrams per kilogram of body weight; and preferably 5 to 10 milligrams per kilogram per day given in divided doses 2 to 4 times a day.

Dosage forms (compositions) suitable for internal administration contain from about 5 milligrams to about 500 milligrams of active ingredient per unit. In these pharmaceutical compositions the active ingredient will ordinarily be present in an amount of about 0.5 - 95% by weight based on the total weight of the composition.

The active ingredient can be administered orally in solid dosage forms, such as capsules and tablets, or in liquid dosage forms, such as suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dixtrose (glucose), and related sugar solutions and glycols such as propylene glycol or polyethylene glycols are suitable carriers for parenteral solutions. Solutions for parenteral administration contain preferably a water-soluble salt of the active ingredient, suitable stabilizing agents, and, if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 200 milligrams of lactose, 30 milligrams of talc, and 10 milligrams magnesium stearate.

Tablets

A large number of tablets are prepared by conventional procedures so that the dosage unit is 250 milligrams of active ingredient, 50 milligrams of ethyl cellulose, 5 milligrams of colloidal silicon dioxide, 5 milligrams of magnesium stearate, 10 milligrams of microcrystalline cellulose, 40 milligrams of cornstarch and 150 milligrams of lactose. Appropriate coatings may be applied to icrease palatability or delay absorption.

Suspension

An aqueous suspension is prepared for oral administration so that each 5 milliliters contain 100 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Use of the esters of this invention as antibacterial agents is exemplified by data for 6,7-methylene-1-(2,2,2-trifluoroethyl)-4(1H)-quinolone-3-carboxylic acid, trimethylacetoxymethyl ester. In vivo determinations of antibacterial activity are carried out in mice.

The test bacterium is growth in bacteriological medium from frozen stock cultures. The culture is centrifuged, resuspended, centrifuged again, resuspended in fresh bacteriological medium, and diluted to the proper infective concentration. Mice are infected by intraperitoneal or intravenous injection of 0.2 ml. of the diluted bacterial culture.

Test compounds are dissolved or suspended in water containing 0.01% Tween 80 by either sonication or bead-milling to break up the materials in order to dissolve them or provide a fine suspension for the insoluble compounds. Concentrations are prepared so that when 0.2 ml. of the solution or suspension is administered to mice orally by intubation, the correct amount of compound in mg/kg of mouse is provided.

The mice are doses with test compound orally by intubation at appropriate intervals following infection and mortality is recorded through the third day. The effective dose 50 ($ED_{50}$) and lethal dose for 50% kill ($LD_{50}$) are calculated by the Reed-Muench method.

Table 1 shows the results of a test in mice infected with *Escherichia coli* by the intraperitoneal route. Compound was administered orally by intubation immediately following infection and again four hours after infection.

Table 2 shows the results for other compounds in the same test.

Table 1

COMPARISONS OF OXOLINIC ACID AND 6,7-METHYLENEDIOXY-1-(2,2,2-TRIFLUOROETHYL)-4(2H)-QUINOLONE-3-CARBOXYLIC ACID TRIMETHYLACETOXYMETHYL ESTER AT TWO E. COLI MOUSE INFECTION LEVELS

| Compound | Mg/Kg[1] PO | 135 $LD_{50}$[2] % Survivors | $ED_{50}$ Mg/Kg | 18 $LD_{50}$[2] % Survivors | $ED_{50}$ Mg/Kg |
|---|---|---|---|---|---|
| 6,7-Methylenedioxy-1-(2,2,2-trifluoroethyl)-4(1H)-quinolone-3-carboxylic acid trimethylacetoxymethyl ester | 10 30 100 | 17 8 50 | 77 | 33 50 75 | 24 |
| Oxolinic Acid | 10 30 100 | 17 17 25 | >100 | 8 33 83 | 45 |
| Control | | 14 | | 14 | |

[1]Animals dosed orally at the time of infection and again four hours later
[2]Determined by agar plate counts and stock culture titration, the dose is the $LD_{50}$ multiplied by the number preceding it.

TABLE 2

| Compound of Example | 2 $LD_{50}$ $ED_{50}$ (mg./kg.) | 4 $LD_{50}$ $ED_{50}$ (mg./kg.) |
|---|---|---|
| 4 | | 73 |
| 5 | | 40 |
| 6 | | 25 |
| 7 | 19 | |
| 8 | 29 | |
| 9 | | 34 |

I claim:
1. A compound of the formula

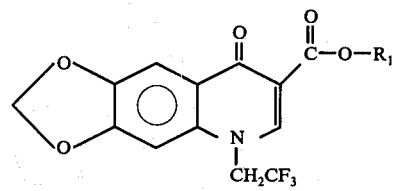

where
$R_1$ = H, alkyl of 1-3 carbons or a univalent cation: $Na^+$, $K^+$, $NH_4^+$, $Li^+$, $\frac{1}{2}Ca^{++}$, $\frac{1}{2}Mg^{++}$.

2. The compound of claim 1 where $R_1$ is H: 6,7-methylenedioxy-1-(2,2,2-trifluoroethyl)-4(1H)-quinolone-3-carboxylic acid.

* * * * *